(12) United States Patent
Kidwell

(10) Patent No.: US 11,885,801 B2
(45) Date of Patent: Jan. 30, 2024

(54) DELAY PROCESS TO PROVIDE TIMED CHEMISTRY TO LATERAL-FLOW IMMUNOASSAYS

(71) Applicant: The Government of the United States of America, as represented by the Secretary of the Navy, Arlington, VA (US)

(72) Inventor: David A. Kidwell, Alexandria, VA (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 135 days.

(21) Appl. No.: 17/407,154

(22) Filed: Aug. 19, 2021

(65) Prior Publication Data
US 2022/0057389 A1 Feb. 24, 2022

Related U.S. Application Data

(60) Provisional application No. 63/068,725, filed on Aug. 21, 2020.

(51) Int. Cl.
*G01N 33/543* (2006.01)
*G01N 33/52* (2006.01)
*G01N 21/29* (2006.01)
*G01N 21/78* (2006.01)

(52) U.S. Cl.
CPC ....... *G01N 33/54388* (2021.08); *G01N 21/29* (2013.01); *G01N 21/78* (2013.01); *G01N 33/525* (2013.01); *G01N 2201/04* (2013.01)

(58) Field of Classification Search
None
See application file for complete search history.

(56) References Cited

U.S. PATENT DOCUMENTS

| | | | |
|---|---|---|---|
| 3,733,213 A | * | 5/1973 | Jacob ................ C23C 18/2086 428/458 |
| 5,200,321 A | | 4/1993 | Kidwell |
| 5,369,007 A | | 11/1994 | Kidwell |
| 5,384,265 A | | 1/1995 | Kidwell et al. |
| 5,637,508 A | | 6/1997 | Kidwell et al. |
| 5,712,170 A | * | 1/1998 | Kouvonen ........... G01N 33/558 436/514 |

(Continued)

OTHER PUBLICATIONS

TechConnect Briefs (Jun. 17, 2019), ISBN 978-0-9988782-8-7 (Year: 2019).*

(Continued)

*Primary Examiner* — Christopher L Chin
*Assistant Examiner* — Estifanos Hailu
(74) *Attorney, Agent, or Firm* — US Naval Research Laboratory; Rebecca L. Forman

(57) ABSTRACT

The present invention provides for a release system for delaying application of chemical reagents in a lateral-flow immunoassay. A chemistry release fiber comprising a permeable membrane and a chemical release agent is used to delay chemical reagent delivery to the indicator of a lateral-flow immunoassay. Also disclosed is the related method of delaying application of chemical reagents in a lateral-flow immunoassay.

6 Claims, 10 Drawing Sheets

(56) References Cited

U.S. PATENT DOCUMENTS

| | | | |
|---|---|---|---|
| 5,726,013 A * | 3/1998 | Clark | B01L 3/5023 436/514 |
| 7,306,780 B1 * | 12/2007 | Kravitz | B01J 19/0093 423/280 |
| 11,209,429 B2 | 12/2021 | Kidwell | |
| 11,293,922 B2 | 4/2022 | Vallejo | |
| 11,340,217 B2 | 5/2022 | Kidwell | |
| 2016/0270389 A1 * | 9/2016 | Glasbey | A01N 59/00 |
| 2019/0339265 A1 | 11/2019 | Kidwell et al. | |

OTHER PUBLICATIONS

Gao et al., "Ultrasensitive Paper Based Nucleic Acid Detection Realized by Three-Dimensional DNA-AuNPs Network Amplification," Biosensors & Bioelectronics, 2017, 92: 529-35.

Fu et al., "Enhanced Sensitivity of Lateral Flow Tests Using a Two-Dimensional Paper Network Format," Analytical Chemistry, 2011, 83 (20): 9741-46.

Lutz et al., "Dissolvable Fluidic Time Delays for Programming Multi-Step Assays in Instrument-Free Paper Diagnostics," Lab on a Chip, 2013, 13 (14): 2840-47.

Rayev et al., "Carbon-Protein Covalent Conjugates in Non-Instrumental Immunodiagnostic Systems," Journal of Immunological Methods, 2008, 336 (August): 9-15.

Han et al., "Three-Dimensional Paper-Based Slip Device for One-Step Point-of-Care Testing," Scientific Reports, 2016, 6 (1): 25710.

Linares et al., "Enhancement of the Detection Limit for Lateral Flow Immunoassays: Evaluation and Comparison of Bioconjugates," Journal of Immunological Methods, 2012, 375 (1-2): 264-70.

Tominaga, "Enhanced Sensitivity of Lateral-Flow Test Strip Immunoassays Using Colloidal Palladium Nanoparticles and Horseradish Peroxidase," LWT—Food Science and Technology, 2017, 86 (August).

Tominaga, "Rapid Detection of Klebsiella Pneumoniae, Klebsiella Oxytoca, Raoultella Ornithinolytica and Other Related Bacteria in Food by Lateral-Flow Test Strip Immunoassays," Journal of Microbiological Methods, 2018, 147 (April): 43-49.

Yang et al., "Gold Nanocage-Based Lateral Flow Immunoassay for Immunoglobulin G," Microchimica Acta, 2017, 184: 2023-29.

Yu et al., "Development of a Rapid Dipstick with Latex Immunochromatographic Assay (DLIA) for Diagnosis of Schistosomiasis Japonica," Parasites & Vectors, 2011, 4 (1): 157.

Zhang et al., "Effect of Different-Sized Gold Nanoflowers on the Detection Performance of Immunochromatographic Assay for Human Chorionic Gonadotropin Detection," Talanta, 2018, 194 (March): 604-10.

* cited by examiner

DELAY PROCESS TO PROVIDE TIMED CHEMISTRY TO LATERAL-FLOW IMMUNOASSAYS

PRIORITY CLAIM

The present application claims the benefit of U.S. Provisional Application No. 63/068,752, filed on Aug. 21, 2020 by David A. Kidwell, entitled "DELAY PROCESS TO PROVIDE TIMED CHEMISTRY TO LATERAL-FLOW IMMUNOASSAYS," the entire contents of which is incorporated herein by reference.

BACKGROUND OF THE INVENTION

Field of the Invention

The present invention relates to providing a delayed release of chemical reagents in lateral-flow immunoassays unencumbered by operator intervention.

Description of the Prior Art

Lateral-flow immunoassays (LFIAs) are common point-of-care (POC) tests for a wide variety of diseases and compounds. The best known are home pregnancy tests. LFIAs have the advantages of rapid results, no required instrumentation, and self-timed due to the capillary flow of the analytes on the strip. LFIAs typically use colored particles as the visual label—most often colloidal gold particles or colored latex that are localized at a line due to a biological binding event (immunocomplex) of the various binding partners—for example antibodies or nucleic acids (Yu et al., "Development of a rapid dipstick with latex immunochromatographic assay (DLIA) for diagnosis of schistosomiasis japonica," *Parasites & Vectors*, 4 (2011) 157-165). The sensitivity of LFIAs is limited by the optical density of the gold label and this sensitivity is inadequate for some applications.

A number of researchers have proposed methods to increase the sensitivity of LFIAs. For example, Zhang, et al. have proposed gold nanoflowers as the labels (Zhang et al., "Effect of different-sized gold nanoflowers on the detection performance of immunochromatographic assay for human chorionic gonadotropin detection," *Talanta* 194 (2019) 604-610)), whereas Yang, et. al. have proposed gold nanocages (Yang et al., "Gold nanocage-based lateral flow immunoassay for immunoglobulin G," *Microchimica Acta* 184, (2017) 2023-2029). Basically, both systems just increase the size of the gold labels and thus show only a modest 2-3 fold increase in sensitivity over conventional labels. Labels other than gold show more promise in increasing sensitivity. For example, Linares, et al., following on the work of Rayev and Shmagel (Rayev et al., "Carbon—protein covalent conjugates in non-instrumental immunodiagnostic systems," *Journal of Immunological Methods*, 336 (2008) 9-15), has reviewed other labels and shown that carbon was about 10 fold more sensitive than gold (Linares et al., "Enhancement of the detection limit for lateral flow immunoassays: Evaluation and comparison of bioconjugates," *Journal of Immunological Methods*, 375 (2012) 264-270).

There is only so much optical density a nanoparticle can have in the size regimen of about 50 nm and carbon, as shown by Linares et al., has reached that limit. One can increase the size of the nanoparticle label and thereby increase the optical density at the expense of performance in the LFIA, but even that has its limits as very large particles will not migrate up the strip under the capillary action of the mobile phase. Alternatively, the size of the gold label can be increased after the biological binding event by forming complexes of complexes at a cost of increased steps for the user (Gao et al., "Ultrasensitive paper based nucleic acid detection realized by three dimensional DNA-AuNPs network amplification," *Biosensors and Bioelectronics*, 92 (2017) 529-535).

To increase the sensitivity of LFIAs further amplification schemes have been proposed to increase the absorbance of the label after biological binding event by precipitation of metal at the site of the label. For example, Han et al. (Han et al., "Three-dimensional paper-based slip device for one-step point-of-care testing," *Scientific Reports*, 6 (2016) 25710) have used the well-known autometallographic process of silver enhancement to enhance the colloidal gold labels detectability three fold. However, this chemical enhancement comes at the cost of increased complexity and user intervention in the LFIA system to delay the chemistry until after the biological events have occurred and the manufacturing difficulties that complexity will entail. Fu et al., have used two-dimensional structures for incorporation of multistep processes for improved sensitivity but at the cost of complex manufacturing (Fu et al., "Enhanced Sensitivity of Lateral Flow Tests Using a Two-Dimensional Paper Network Format," *Anal. Chem.*, 83 (2011) 7941-7946).

To increase the sensitivity of LFIAs, other amplification schemes have been proposed to precipitate a dye at the site of the label. Building on much earlier catalytic work of Kidwell and Conyers (Kidwell et al., "Catalytic particles as replacements for enzymes in immunoassays and DNA Assays," U.S. Pat. No. 5,384,265 issued Jan. 24, 1995 and Kidwell et al., "Biomolecules bound to polymer or copolymer coated catalytic inorganic particles, immunoassays using the same and kits containing the same," U.S. Pat. No. 5,637,508 issued Jun. 10, 1997), Kidwell has shown that appropriate dye systems and selected nanoparticles can enhance the sensitivity of LFIAs more than 1000 fold over gold labels (Kidwell et al., "Catalytic Nanoparticles to Enhance the Sensitivity of Lateral Flow Immunoassays," Nanotech 2019 Conference and Exposition, Boston, MA, Jun. 17, 2019; Kidwell, "Catalytic Particles for Increased Sensitivity in Lateral Flow Immunoassays," United States Patent Application 20180052153, Feb. 22, 2018; and Kidwell, "Catalytic Signal Enhancement for Lateral Flow Immunoassays," United States Patent Application 20190391138, Dec. 26, 2019). Tominaga has used both enzymatic catalysts as well as chemical catalysts to localize a dye at the site of the label by manually applying a substrate after the biological event has occurred (Tominaga, "Enhanced sensitivity of lateral-flow test strip immunoassays using colloidal palladium nanoparticles and horseradish peroxidase," *LWT—Food Science and Technology*, 86 (2017) 566e570 and Tominaga, "Rapid detection of *Klebsiella pneumoniae, Klebsiella oxytoca, Raoultella ornithinolytica* and other related bacteria in food by lateral-flow test strip immunoassays," *Journal of Microbiological Methods*, 147 (2018) 43-49).

As was shown by the work of Kidwell, catalytic LFIA systems have a considerable sensitivity advantage over colorimetric labels. If the substrate of the catalyst is applied contemporaneously with the analyte solution, the catalyst will start developing the dye system (catalytic chemistry or substrate chemistry) thereby precipitating the dye along the strip as the capillary flow occurs. Thus, the substrate chemistry needs to be delayed until after the biological binding event and preferably after all the excess catalyst is wicked from the strip into the top absorbent pad. Delaying the substrate chemistry also has the advantage that the reagents need not be compatible to biology as often once the nanoparticle labels are localized by biology, they are strongly bound and hard to remove. Thus, unusual pH or strong oxidizing or reducing conditions can be used to optimize the catalyst activity rather than optimizing the biological activity of the binding partners.

As exemplified by Tominaga, a user could manually expose the developed strip to the catalytic chemistry, but this approach requires user interaction as well as separate packaging for the reagents. As exemplified by Fu, et al., the delay could be accomplished by having a two arm structure with one arm longer than the other and the length corresponding to a delay. Timing is limited as longer flow channels require more solution for filling. Additionally, this form often requires that the user of the LFIA place different solutions in different wells of the LFIA device and thus increases the complexity of handling as well as the need for several solutions, which either must be packaged separately or have an interior package broken the user. Both schemes increasing the complexity and manufacturing cost. Another approach is to provide a diffusion barrier as exemplified by Kidwell, where timing is determined by the porosity of the barrier (Kidwell, "Microassay on a Card," U.S. Pat. No. 5,200,321 issued on Apr. 6, 1993 and Kidwell, "Microassay on a Card," U.S. Pat. No. 5,369,007 issued on Nov. 29, 1994). Timing can be varied over a wide range as the diffusion can be adjusted due to pore size and pore density of the barrier. This would again require two wells—one for application of the sample and another for application of the solution to dissolve the reagents—although these solutions could be identical. An alternative to a diffusion barrier is a dissolving barrier as exemplified by Lutz et al. (Lutz et al., "Dissolvable fluidic time delays for programming multistep assays in instrument-free paper diagnostics," *Lab Chip*, 13 (2013) 2840-2847). This also has the advantage that the timing can be varied but it exposes the strip and catalyst to whatever the material is used to produce the barrier. For example, if dissolving glucose is used as the barrier, the strip and catalyst would be exposed to a saturated solution of glucose, which can affect the subsequent chemistry or even release of the biological binding pair. Another alternative is varying the pressure on individual wells as exemplified by Lawrence, et al. (Lawrence et al., Sequential Lateral Flow Device, United States Patent Application 20190079085). The method of Lawrence et al. could be thought of as equivalent to having variable diffusion barriers where the diffusion is controlled by squeezing a sponge, which changes the pore size and diffusion rate.

BRIEF SUMMARY OF THE INVENTION

The present invention provides a system and method to provide delayed release of chemical reagents in LFIAs. A chemistry release fiber comprising a permeable membrane and a chemical release agent used to delay chemical reagent delivery to the indicator of a catalytically-enhanced LFIA (cLFIA). This enables one-step cLFIA devices that are simple to use and have substantially improved sensitivity.

It is a goal of the present invention to delay the introduction of the catalytic substrates until after the biological immunochemistry has occurred without user intervention—all timing is accomplished by the design of the LFIA. It is a further goal of the present invention to provide this delay in easily manufactured form that is adaptable to a number of LFIA formats and does not expose the strip or catalyst to unnecessary reagents. It is another goal of the present invention to provide a system where the chemistry can be varied to act with multiple catalysts and enzymes used as labels.

These and other features and advantages of the invention, as well as the invention itself, will become better understood by reference to the following detailed description, appended claims, and accompanying drawings.

DETAILED DESCRIPTION OF THE INVENTION

The present invention provides a delayed release of chemical reagents in LFIAs. The LFIAs have a chemistry release fiber comprising a permeable membrane and an absorbent material having a chemical release agent. The chemistry release fiber delays chemical reagent delivery to the indicator of the LFIA.

Figure 1:
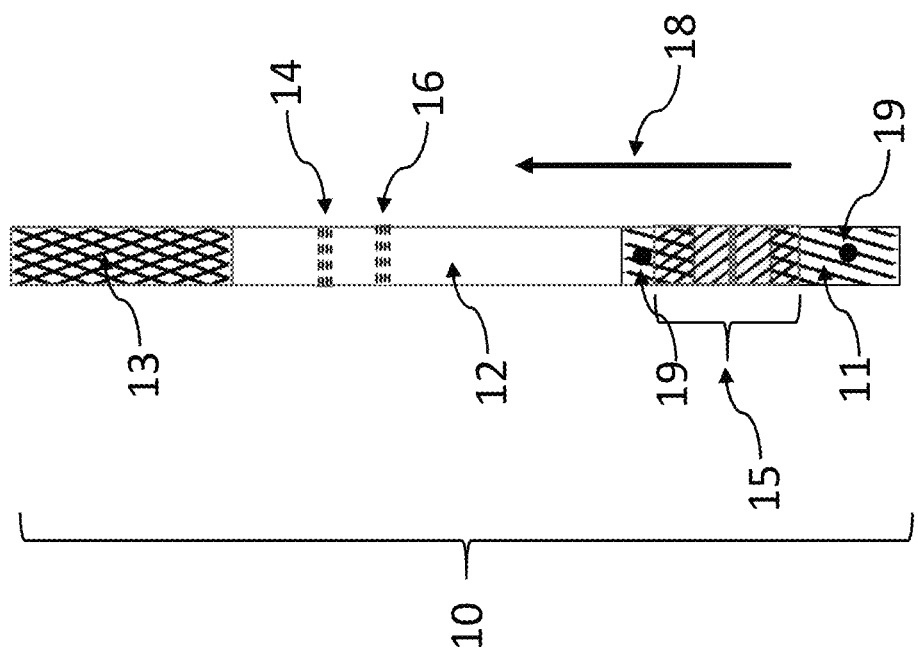
FIG. 1 is a top view of a lateral-flow immunoassay containing a chemical release fiber construct in accordance with the teachings of the present disclosure.

One embodiment of the invention is shown in FIG. 1, which depicts a top view of a lateral-flow immunoassay construct 10. On the lateral-flow immunoassay construct 10 is the chemical release fiber construct 15. The lateral-flow immunoassay construct 10 comprises a conjugate pad 11, plastic-backed nitrocellulose 12, and an absorption pad 13. A capture line 16 comprising biotinylated bovine serum albumin is absorbed to the plastic-backed nitrocellulose 12. A control line 14 comprising bovine serum albumin is absorbed to the plastic-backed nitrocellulose 12. The catalyst 19 used as the visualization label in the assay is initially absorbed onto pad 11. A plurality of catalyst 19 particles are present. Catalyst 19 may be below, under, or above (as measured by the liquid flow in the lateral-flow construct 10, which is from pad 11 to pad 13) the chemical release fiber construct 15. Since the catalyst 19 comprises nanosized particles, they are not individually visible. The size indicated for catalyst 19 in FIG. 1 is only for illustrative purposes. The general liquid flow is indicated by arrow 18.

Figure 2:
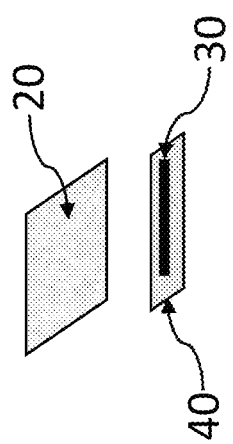
FIG. 2 is a cross-sectional view of a chemical release fiber construct in accordance with the teachings of the present disclosure.

FIG. 2 displays a side view of one inner construction of the chemical release fiber construct 15. The chemical release fiber construct 15 in one embodiment is a three layer device comprising a tape overlay 20, a fiber 30, and the permeable membrane 40. Fiber 30 is impregnated with chemical precursors, buffers, and stabilizing agents necessary for the particular catalyst 19, used as a label, to function. The permeable membrane 40 acts to delay the diffusion of water into fiber 30 and the diffusion out of the reagents that are contained on or in fiber 30 and are thereby dissolved from the fiber. The tape overlay 20 acts to hold the fiber 30 in contact with membrane 40 and the whole construct in contact with either the conjugate pad 11 or the nitrocellulose membrane 12. The placement of chemical release fiber construct 15 is in no way limiting. Having construct 15 in contact with the nitrocellulose membrane 40 is preferred. Having chemical release fiber construct 15 in contact with conjugate pad 11 is most preferred. Other types of lateral-flow assays, known in the art, have additional layers to act as filters for whole blood, for example, and placing chemical release fiber construct 15 on one of those additional layers may be advantageous. The number of fibers, as exemplified by a single fiber 30 are by no means limiting to the chemical release fiber construct 15. Chemical release fiber construct 15 can have a plurality of fibers encompassing the chemistry required for the detection system. Additionally, several chemical release fibers may be used to separate and control the timing of various reagents needed for the visualization of the catalyst label 19 to function. Membrane 40 controls diffusion of liquid from part of a flowing stream diffusion though capillary action in nitrocellulose 12 and conjugate pad 11 into the absorbent material via capillary action and the absorbent material releases reagents that then diffuse back through the membrane into the main flowing stream via simple diffusion. Capillary action is faster than simple diffusion due to convection caused by the absorption of liquid.

Figure 3:
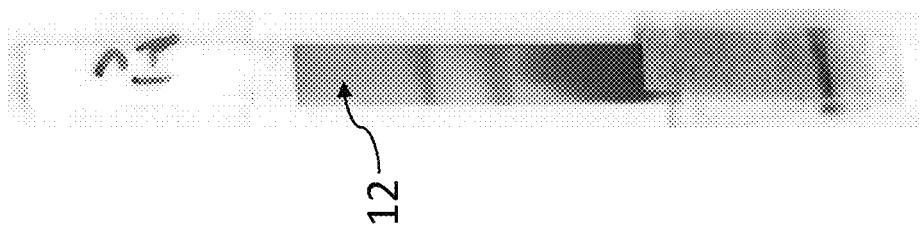
FIG. 3 is a photograph of a lateral-flow immunoassay where the chemical reagents were released at the same time as the catalyst.

Depicted in FIG. 3 is an example of a lateral-flow immunoassay where the initial immunochemistry and chemical release are contemporaneous. FIG. 3. shows the large background caused by the catalyst label 19 interacting with the chemistry while the label migrates up the nitrocellulose stip.

Figure 4:
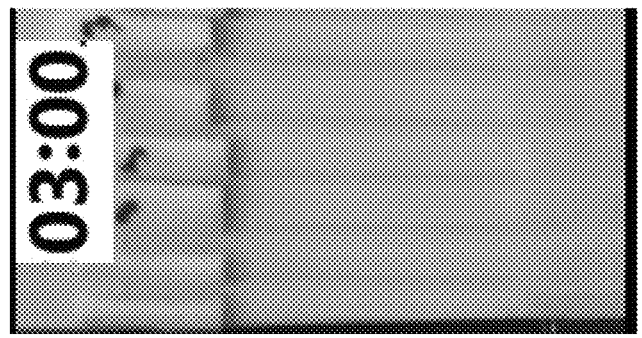
FIG. 4 is a photograph of six lateral-flow immunoassays run in parallel where the initial immunochemistry has migrated and the release of reagents from the chemical release fiber construct has just begun.

FIG. 4 shows a photograph of six lateral-flow immunoassays run in parallel where the initial immunochemistry has migrated and the release of reagents from the chemical release fiber construct has just begun. The photograph is from a time-lapsed movie where the time indicated is from the initial application of the mobile liquid. The immobilized catalytic particles are not visible due to their low concentration.

Figure 5:
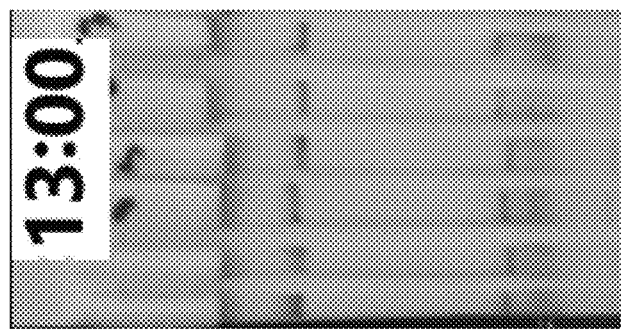
FIG. 5 is a photograph of six lateral-flow immunoassays run in parallel where the initial immunochemistry has migrated and the release of reagents from the chemical release fiber construct has completed.

FIG. 5 shows a photograph of six lateral-flow immunoassays run in parallel where the initial immunochemistry has migrated and the release of reagents from the chemical release fiber construct has completed. The figure is from a time-lapsed movie where the time indicated is from the initial application of the mobile liquid. The localization of the developed dye by the catalytic particles is clearly visible.

Figure 6:
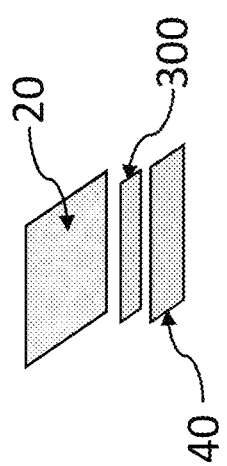
FIG. 6 is a cross-sectional view of a chemical release fiber construct in accordance with the teachings of the present disclosure.

FIG. 6 shows an embodiment of the inner construction of the chemical release fiber construct. Chemical release fiber construct comprises the tape overlay 20, a pad 300 containing the chemicals of interest, and the permeable membrane 40. Pad 300 is impregnated with chemical precursors, buffers, and stabilizing agents necessary for the particular catalyst used as a label to function. However, a fiber or fibers are preferred if the amount of chemicals necessary is small. The number of pads, as exemplified by pad 300 is no means limiting to the chemical release fiber construct 150. Chemical release fiber construct 150 can have a plurality of pads 300 and fibers 30 containing the chemistry required for the detection system. Fibers are preferred over pads if the amount of chemicals necessary is small since less liquid need be diverted from the lateral-flow channel into the chemical release fiber to moisten and saturate fibers as compared to pads.

The mechanism for delay of release of materials from the chemical release fiber construct is thought to occur with the fluid traveling up the nitrocellulose strip 12 and through the conjugate pad 13, may travel due to capillary action of the substrate. Capillary action causes rapid movement of molecules because of convection. However, flow in the nitrocellulose strip 12 is nearly laminar such that mixing side to side and up and down (in the direction of flow indicated by arrow 19) is minimal. Likewise diffusion up through membrane 40 is primarily by capillary action due to absorption of the fluid by fiber 30 and or pad 300 causing convection of the fluid into the chemical release fiber construct. This fluid convection is limited by the hydrophobicity and wetting of membrane 40. Once the fluid exceeds the absorptive capability of the components of the chemical release fiber construct, then convection stops and back diffusion through membrane 40 can occur. However, as convection is minimized since there is no wicking action as all components are saturated with liquid, this back diffusion could be considered as pure diffusion. Pure diffusion is much slower than convection and slows the rate of introduction of any materials released from the interior of the chemical release fiber construct.

Variable delay can be achieved by increasing the absorptive capacity of the chemical release fiber construct by increasing the number or size of absorptive entities present. These entities may contain useful chemistry or may be contain no chemistry and are just inert delay entities. One method could be to place a sheet of filter paper between membrane 40 and fiber 30. Another method could be to wrap one or more of the fibers in an absorptive material to delay the release of chemistry from that fiber over release from other fibers.

Additional delay can be achieved by varying the contact area of membrane 40 with smaller contacts increasing the delay. This is less desirable because a smaller contact area will also decrease the application of dissolved materials released from the interior back into the flowing stream. Likewise, increasing the delay by decreasing the diffusion though membrane 40 through, for example, decreasing the pore size, number or pores, thickness, or hydrophobicity would also decrease the rate of the back diffusion of dissolved materials released from the interior absorptive units back into the flowing stream, which may be advantageous. However, modulating the delay by varying the absorptive capability of the interior of the chemical release fiber construct is preferred. Likewise, modulating the delay by varying the membrane thickness is most preferred.

Example 1

Two fibers are used as fiber 30. One is impregnated with a hydrogen peroxide precursor that releases hydrogen peroxide upon exposure to water. The second fiber (not shown in FIG. 1) is impregnated with two dye precursors that are for precipitating dye in the presence of a catalyst. This example uses catalyst dye chemistry impregnated on the second fiber as outlined by Kidwell (Kidwell, "Catalytic Particles for Increased Sensitivity in Lateral Flow Immunoassays," United States Patent Application 20180052153, Feb. 22, 2018 and Kidwell et al., "Catalytic Particles For Signal Enhancement For Lateral Flow Immunoassays," United States Patent Application 20190339265, Nov. 7, 2019).

The second fiber was prepared by soaking cotton twine (average 225 μm diameter) in a solution of 40 mg/mL 4-Hydroxy-1-naphthalenesulfonic acid sodium salt (CAS #6099-57-6), 30 mg/mL N,N-Diethyl-p-phenylenediamine (CAS #6283-63-2), and 20 mg/mL citric acid (CAS #77-92-9) in equal parts ethanol and water. Fiber 30 was prepared by soaking a second piece of cotton twine in a four parts to one solution of 1M sodium carbonate buffer and concentrated hydrogen peroxide (30% H2O2 in H2O). Soaking solutions were used in volumes that well exceeded the saturation volume for the length of string so as to not limit the quantity of chemical absorbed. After 5 minutes exposure to each solution, each piece of twine was air dried. The two dried strings were placed side by side, centered on a piece of overlay adhesive 10 (Oracal 651) about 1 cm in width. A 0.5 cm in width polyester tack-etched membrane (Osmonics Poretics 3 μm, cat #33083, typical published water flow rate of 600 mL/min/cm2 at 10 PSI pressure differential) served as permeable membrane 40 and was placed overtop the two fibers. The adhesive 10 overlapping either side of the nylon mesh was then used for assembling the lateral-flow strip.

The overlay adhesive 10 may be eliminated with an appropriate holder pressing the components of fiber 30 or pad 300, membrane 40, and absorption pad 13 or outer suitable backing. However, generally LFIAs are constructed in long or continuous strips that are guillotined into individual strips afterwards and then placed in a holder. Most conveniently, the chemical release fiber construct 15 with adhesive 10 can be applied to the long strip where the adhesive 10 holds the assembly together before individual strips are cut and packaged. This aids in manufacture and changes the manufacturing process very little from LFIAs without the chemical release fiber construct.

Neutravidin palladium conjugates were used as the catalyst. They were prepared by combining 18 μL of PdCl2 (64.4 mM), 182 μL of Neutravidin (2 mg/mL), and 970 μL of distilled water in a microfuge tube. The solution equilibrated for 10 minutes before rapidly adding 30 μL sodium borohydride (10 mg/mL) with vigorous agitation. The solution immediately changed from a pale yellow to brown/gray color upon addition of the reductant. The microfuge tube was placed on a shaking table for a minimum of one hour to allow the reaction to go to completion. The reaction produced protein conjugates with ~2 nm Pd nanoparticles, as measured by transmission electron microscopy. This catalyst was used as catalyst label 19.

A long lateral-flow master card was assembled on 60 mm×30 mm backing cards. First the nitrocellulose 12 (Unisart CN 95 nitrocellulose), arrayed with capture line 16 and control line 14 on a BioDot Xyz printer, was placed length wise in the middle of the card yielding a 25 mm wide area. Next the conjugate strip 11 (Ahlstrom-Munksjo 8964) 20 mm in width and arrayed with dried catalyst 19 was placed at the bottom of the card overlapping nitrocellulose strip 12 by 2-3 mm. The absorption pad 13 (Whatman 50/P blotting paper), cut to 15 mm wide, was placed at the top of the card and overlapped the nitrocellulose 12 by 2-3 mm. The chemical release fiber construct 15, was then placed on top of the conjugate pad such that it was below the dried catalyst label 19 and above the bottom of the strip using the overlapping adhesive 10 to secure it in place. Finally, the assembled lateral-flow strip master card was cut into individual 4 mm wide lateral-flow test strips using a BioDot guillotine cutter.

The results of running the assembled latter-flow strips are shown in FIGS. 4 and 5. This chemical release fiber conjugate, provided a satisfactory delay for all the catalyst label 19 to migrate up the strip. The delay, as measured by time-lapse photography was 3-4 minutes from the start of the test where it took approximately 30 seconds for the liquid line to reach capture line 16. Note the dye development at the boundary of conjugate pad 11 and nitrocellulose 12. This is caused by catalyst 19 being trapped at this boundary and not migrating up the strip. This development is not due to the delay of the chemistry from the chemical release fiber construct 15 being insufficient as demonstrated in FIG. 3.

Example 2

A method to easily visualize the working of the chemical release fiber construct 15 is to use precursors that form a dye upon reaction with a catalyst. It is especially useful to use precursors for the reaction of hydrogen peroxide in the presence of a palladium catalyst. Fiber 30 was constructed as in Example 1. Five different types of chemical release fiber constructs 15, done in triplicate, were constructed with different membranes 40. The constructs were placed on the nitrocellulose strip 12. The average time to just start the development of the line at the catalyst are shown in Table 1 for various chemical release fiber constructs 15. As can be seen in Table 1, the time can be varied over a long period though simply changing the membrane or the number of layers.

TABLE 1

Time to just observe the start of dye formation.

| Construct of Membrane 40 | Time to Start of Dye Formation (minutes) |
|---|---|
| No membrane 40 used | 2.25 |
| 3 μm Nucleophore membrane | 3.92 |
| 0.8 μm Nucleophore membrane | 3.40 |
| 0.2 μm Nucleophore membrane | 7.59 |
| Whatman 1 filter paper | 11.61 |
| 3 μm Nucleophore membrane + Whatman 1 filter paper | 7.41 |

The running solution was 1% hydrogen peroxide in 100 mM sodium carbonate buffer.
The catalyst was sprayed at approximately 30 ng/line.

Example 3

An additional method to easily visualize the working of the chemical release fiber construct 15 is to use colored dyes.

It is especially useful to use anionic dyes as they have less affinity for the components of the chemical release fiber construct 15 and the lateral-flow immunoassay construct 10. pH sensitive dyes such as bromophenol blue are preferred as they change color form yellow to blue on a pH shift. The dye is loaded in fiber 30 in acid media and dried, the fiber will be yellow in color. If the test solution were basic, the rate of hydration of the fiber can be readily measured by the color change. Likewise, the release of the now blue dye into the flowing stream on nitrocellulose 12 can be easily visualized.

FIG. 7A is a photograph of a chemical release fiber construct 15 directly on nitrocellulose 12 after the interior fiber 20 has just been hydrated. FIG. 7B is a photograph of a chemical release fiber construct 15 directly on nitrocellulose 12 during the release of the now blue bromophenol blue dye onto the nitrocellulose. Colloidal gold 190 migrating up the nitrocellulose strip causes a red color. The colloidal gold is labeled with antibodies to human chorionic gonadotropin (hCG) hormone and recovered from commercial hCG tests. The colloidal gold flows under the chemical release fiber construct 15 and is captured on control line 140, striped with goat anti-mouse antibodies. This example demonstrates that chemical release fiber construct 15 does not alter the flow of the colloidal labels on the nitrocellulose and thus can be placed in any location required on the lateral flow system. This example also illustrates that the time of release of the blue dye can be adjusted until after the labeled particles are captured and the excess removed from nitrocellulose strip 12 into absorption pad 13. Six different types of chemical release fiber constructs 15 were constructed with different membranes 40. The membrane 40 pairs left to right are given in Table 2. Referring to Table 2, chemical release fiber constructs 1-3 appeared optimal, with construct 2 being preferred and constructs 4-6 being longer than necessary for the colloidal gold to clear the nitrocellulose strip 12.

TABLE 2

Figure 7:
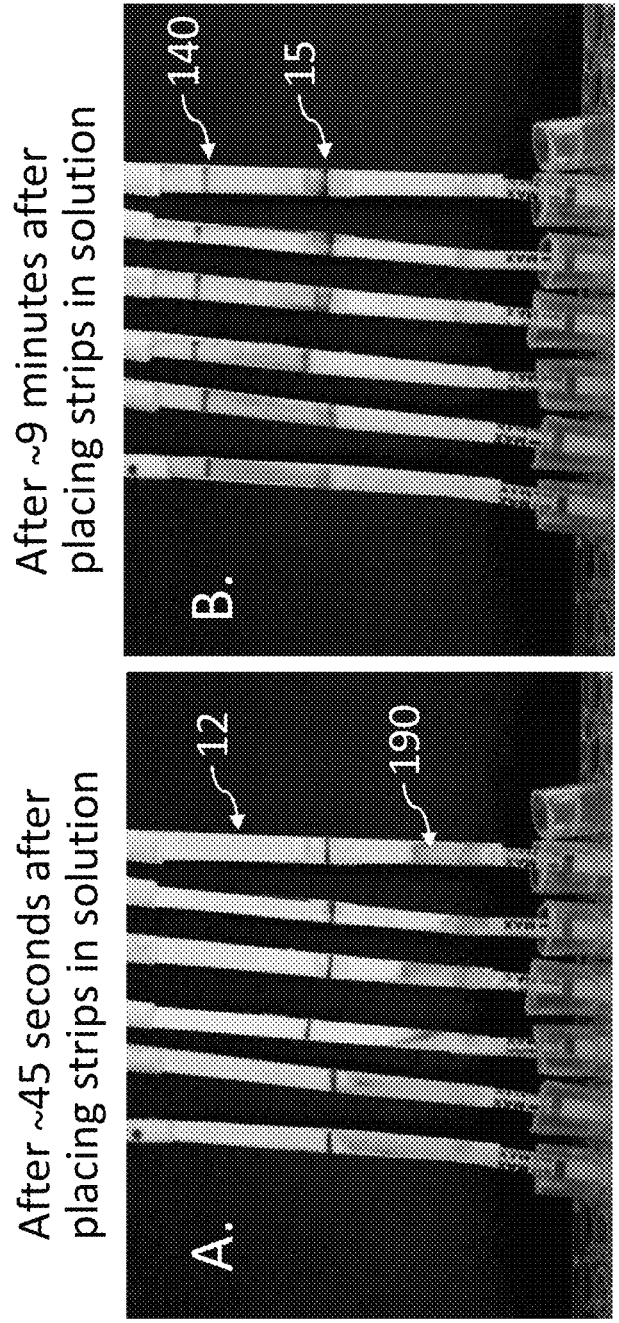
FIG. 7A is a photograph of three different types of chemical release fiber constructs, done in duplicate, constructed in accordance with the teachings of the present disclosure shown after 45 seconds of placing strips in solution.
FIG. 7B is a photograph of the same three different types of chemical release fiber constructs as in FIG. 7A, done in duplicate, constructed in accordance with the teachings of the present disclosure shown after 9 minutes of placing strips in solution.

Components of CRF constructs 15 used in FIG. 7.

| | |
|---|---|
| 1 | Whatman Q8 filter paper as membrane 40, 5 mm wide, 2 cm tape overlay 20 |
| 2 | Whatman Q8 filter paper as membrane 40, 3 mm wide, 2 cm tape overlay 20 |
| 3 | Whatman Q8 filter paper as membrane 40, 3 mm wide, 2 cm tape overlay 20 |
| 4 | Whatman Q8 filter paper soaked in saturated sucrose and air dried as membrane 40, 4 mm wide, 2 cm tape overlay 20 |
| 5 | Whatman Q8 filter paper soaked in saturated sucrose and air dried as membrane 40, 7 mm wide, 2 cm tape overlay 20 |
| 6 | Whatman Q8 filter paper soaked in saturated sucrose and air dried as membrane 40, 7 mm wide, 1 cm tape overlay 20 |

All fiber 20 were the same containing bromophenol blue dye.

Example 4

Figure 8:
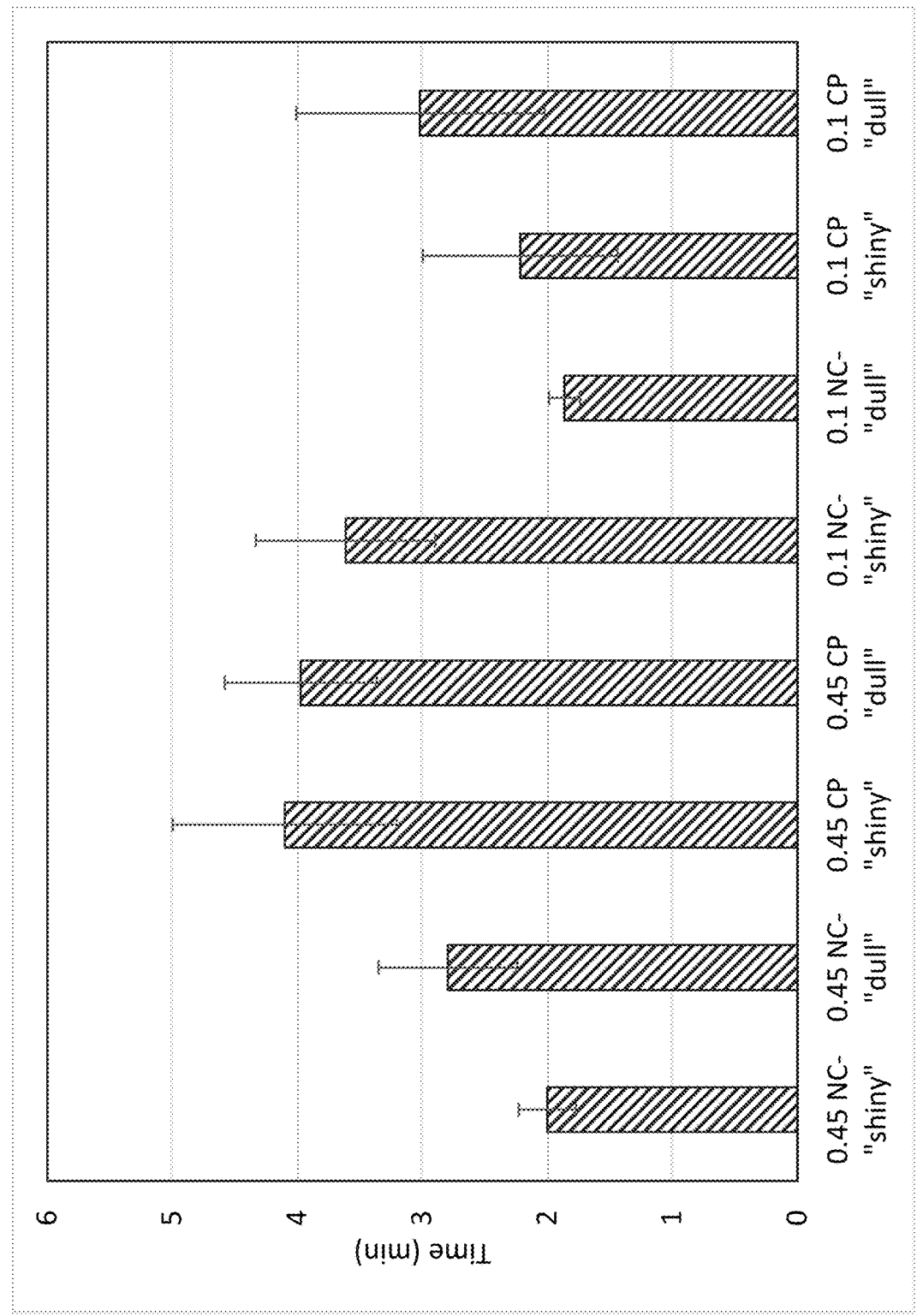
FIG. 8 is a graph showing the time delay using polysulfone membranes as the surface membrane in the chemical release fiber.
Figure 9:
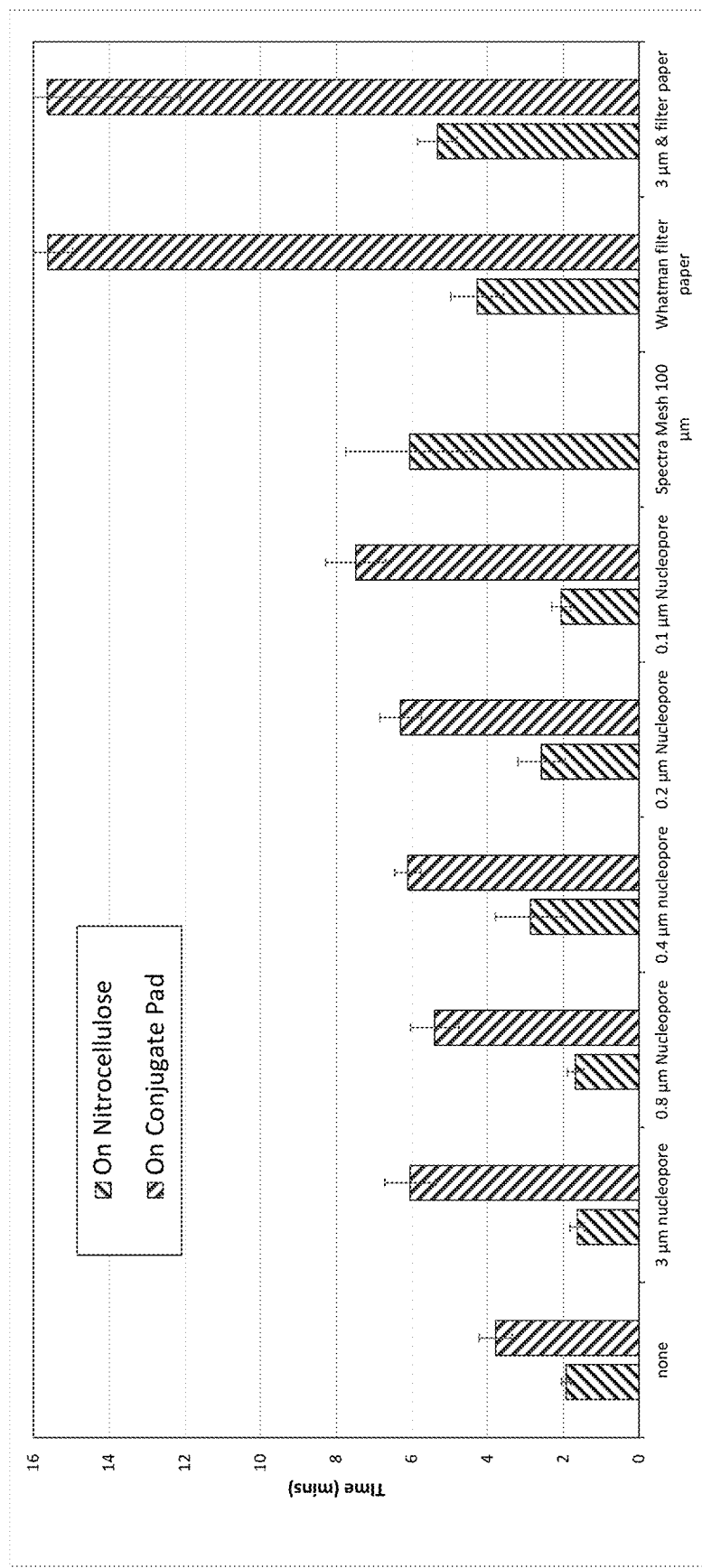
FIG. 9 is a graph showing the time delay using a polycarbonate membrane, nylon mesh, or filter paper membrane as the surface membrane in the chemical release fiber.
Figure 10:
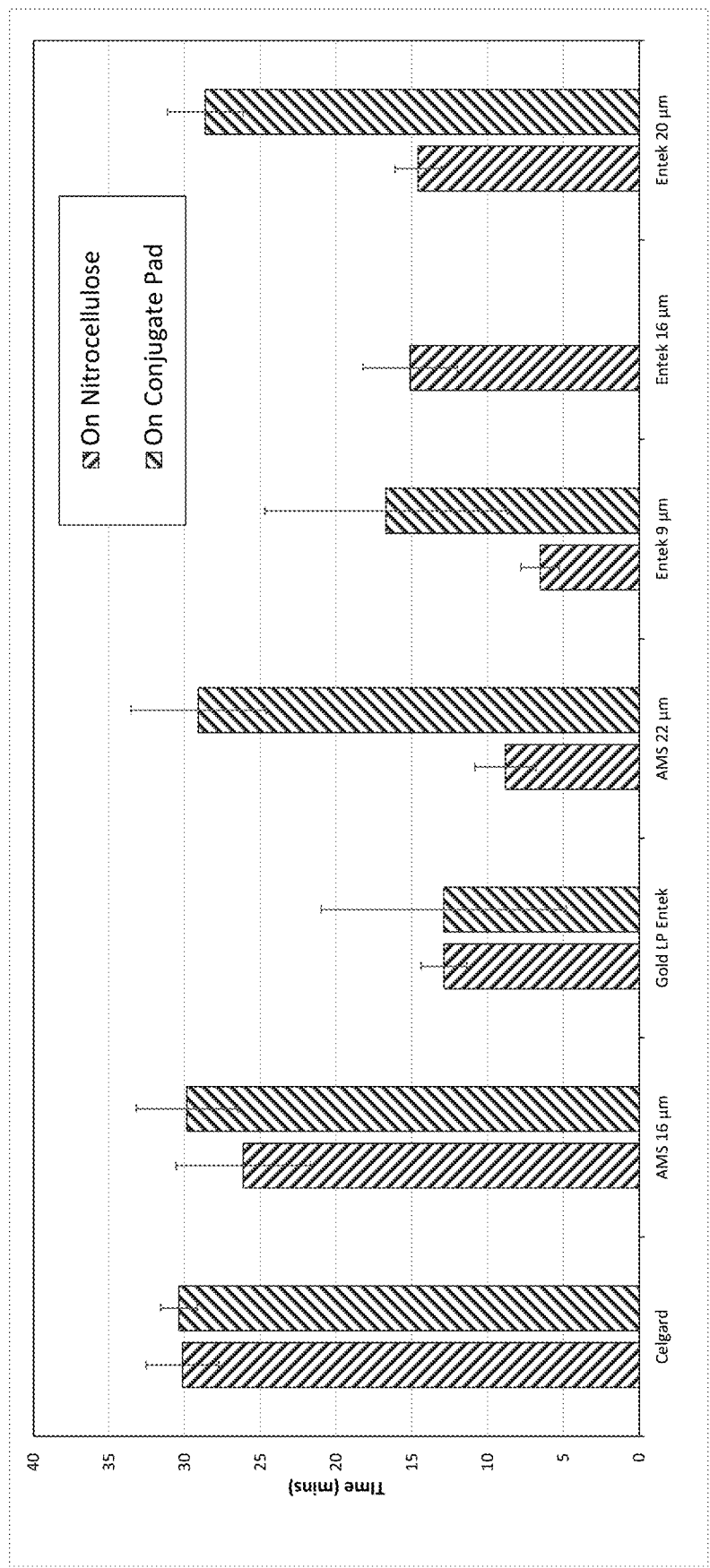
FIG. 10 is a graph showing the time delay using battery separators as the surface membrane in the chemical release fiber.

A number of different membranes were tried in the membrane part of the chemical release fiber construct 15 as shown in FIGS. 8-10. The time delay was measured in a number of replicates simultaneously by placing the LFIA in a tray where the capture line consisted of the palladium nanoparticle catalyst attached to a protein already in place. This scheme was used to measure only the delay and separate the required biology from the chemistry. In these measurements, the chemical release fiber comprised only two color forming reagents. The mobile phase was 1% hydrogen peroxide in 100 mM sodium carbonate buffer. The strips were video recorded and the time difference for the reagents in the chemical release fiber to reach the strip measured by eye after viewing the video where the initial blue color just appeared compared to addition of the buffer-hydrogen peroxide. For some measurements, the video was digitized and each frame examined and the color density calculated over a selected area. The color intensity was plotted vs. time and generally two lines emerged. The intersection of these two lines provided the first indication of the color formation. This process was more cumbersome than the visual process and produced similar results.

FIG. 8 shows the time delay with using polysulfone membranes as the surface membrane 40 in the chemical release fiber. The polysulfone membranes were the hydrophilic type and purchased from Schluicher & Schuell as Catalog #28260 for 0.45 μm pore size membranes or Catalog #28340 for 0.1 μm pore size membranes. The NC refers to application of the polysulfone membranes onto the nitrocellulose part of the LFIA. The CP refers to application of the membrane-CRF construct to the conjugate pad. "Shiny" refers to placing the polysulfone membrane shiny side in contact with the nitrocellulose membrane or with the conjugate pad. "Dull" refers to placing the dull side to the respective surface. The error bars are one standard deviation for between 5-10 measurements.

FIG. 9 shows the time delay with using polycarbonate, nylon mesh, or filter paper membranes as the surface membrane 40 in the chemical release fiber. The polycarbonate membranes were purchased from Nucleophore Corporation, Pleasanton, CA in the indicated pore size. Spectra/mesh was purchased from Spectrum, Houston, TX as the woven nylon type. The filter paper was Whatman® #1 purchased from Whatman International Limited, Maidstone, England. The membrane-chemical release fiber constructs were applied to either the nitrocellulose or conjugate pad. For the polycarbonate membranes, little delay is observed on the nitrocellulose pad as compared to a chemical release fiber without a membrane. The error bars are one standard deviation for between 5-10 measurements.

FIG. 10 shows the time delay with using battery separators as the surface membrane 40 in the chemical release fiber. The Entek membranes were from Entek Corporation, Lebanon, OR and were the thickness indicated. The Celgard membrane was from Celgard, LLC., Charlotte, NC The AMS membrane was from AMS Technologies Ltd.; Yehuda, Israel. The membrane-chemical release fiber constructs were applied to either the nitrocellulose or conjugate pad. The error bars are one standard deviation for between 5-10 measurements. Values greater than 30 minutes indicate that the delay was at least 30 minutes.

Another embodiment of the present invention is to employ two or more chemical release fiber constructs 15 for delivery of pulsed chemistry to the biologically immobilized catalyst.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A release system for delaying application of a chemical reagent to a lateral-flow immunoassay, comprising:
   a membrane;

an absorbent material containing a chemical reagent;
    wherein the absorbent material comprises absorbed color forming reagents;
an adhesive covering; and
wherein the absorbed color forming reagents comprises a phenylenediamine salt with a napthol or a phenol.

2. The release system of claim 1, wherein the membrane comprises a porous polymer.

3. The release system in claim 1, wherein the membrane comprises a fibrous material.

4. The release system of claim 1, wherein the absorbent material comprises an absorbent pad.

5. The release system of claim 1, wherein the absorbent material comprises an absorbent string.

6. The release system of claim 1, wherein the absorbent material comprises a plurality of absorbent strings, absorbent pads, or any combination thereof.

* * * * *